United States Patent
Mundschau et al.

(10) Patent No.: US 9,949,906 B2
(45) Date of Patent: *Apr. 24, 2018

(54) SUBSTRATES HAVING FORMULATIONS WITH IMPROVED TRANSFERABILITY

(75) Inventors: Stacy Averic Mundschau, Weyauwega, WI (US); Scott W. Wenzel, Neenah, WI (US); Lisa Ann Flugge-Berendes, Appleton, WI (US); Jonathan Kyle Arendt, New London, WI (US); Kroy Donald Johnson, Neenah, WI (US); Bernard J. Minerath, III, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 470 days.

This patent is subject to a terminal disclaimer.

(21) Appl. No.: 12/172,049

(22) Filed: Jul. 11, 2008

(65) Prior Publication Data

US 2010/0008958 A1    Jan. 14, 2010

(51) Int. Cl.
| | |
|---|---|
| *A61K 8/31* | (2006.01) |
| *A61K 8/06* | (2006.01) |
| *A61K 8/34* | (2006.01) |
| *A61K 8/37* | (2006.01) |
| *A61K 8/72* | (2006.01) |
| *A61K 8/891* | (2006.01) |
| *A61K 8/02* | (2006.01) |

(52) U.S. Cl.
CPC .............. *A61K 8/31* (2013.01); *A61K 8/0208* (2013.01); *A61K 8/06* (2013.01); *A61K 8/345* (2013.01); *A61K 8/37* (2013.01); *A61K 8/72* (2013.01); *A61K 8/891* (2013.01)

(58) Field of Classification Search
CPC ......... A61B 42/00; A61B 42/60; A61B 42/10; A61L 31/16; A61L 31/18; A61L 2300/452; A61L 2300/30; A61L 2300/606; A61L 15/225; A61L 31/14; A61L 31/005; A61L 31/141; A61L 31/145; A61L 2300/428; A61Q 19/00; A61Q 19/10; A61Q 17/04; A61Q 19/007; A61Q 15/00; A61Q 17/00; A61Q 17/005; A61Q 19/02; A61Q 19/04; A61Q 19/06; A61Q 1/02; A61Q 1/06; A61Q 5/00; A61Q 5/02; A61Q 5/08; A61Q 5/10; A61Q 5/12; A61K 8/0208; A61K 2300/00; A61K 8/345; A61K 31/45; A61K 31/70; A61K 8/365; A61K 8/60; A61K 2800/412; A61K 2800/5922; A61K 8/06; A61K 8/062; A61K 8/11; A61K 8/31; A61K 8/42; A61K 8/8152; A61K 8/85; A61K 8/898; A61K 9/0014; A61K 9/70; A61K 9/7061; A61K 9/7069; A61K 9/7084; A61K 2800/5426; A61K 2800/77; A61K 2800/782; A61K 2800/87; A61K 2800/88; A61K 31/045; A61K 31/7012; A61K 38/1825; A61K 38/47; A61K 47/06; A61K 47/20; A61K 47/24; A61K 47/26; A61K 47/30; A61K 47/34; A61K 8/02; A61K 8/0204; A61K 8/0237; A61K 8/29; A61K 8/34; A61K 8/416; A61K 8/4913; A61K 8/553; A61K 8/63; A61K 8/678; A61K 8/86; A61K 8/89; A61K 8/891; A61K 8/97; A61K 9/0019; A61K 9/107; A61K 9/19

See application file for complete search history.

(56) References Cited

U.S. PATENT DOCUMENTS

| | | |
|---|---|---|
| 3,301,746 A | 1/1967 | Sanford et al. |
| 3,338,992 A | 8/1967 | Kinney |
| 3,341,394 A | 9/1967 | Kinney |
| 3,473,576 A | 10/1969 | Amneus |
| 3,502,763 A | 3/1970 | Hartmann |
| 3,542,615 A | 11/1970 | Dobo et al. |
| 3,573,164 A | 3/1971 | Friedberg et al. |
| 3,675,121 A | 7/1972 | Thompson |
| 3,692,618 A | 9/1972 | Dorschner et al. |
| 3,802,817 A | 4/1974 | Matsuki et al. |
| 3,812,000 A | 5/1974 | Salvucci, Jr. et al. |
| 3,821,068 A | 6/1974 | Shaw |
| 3,849,241 A | 11/1974 | Butin et al. |
| 3,896,807 A | 7/1975 | Buchalter |
| 3,974,025 A | 8/1976 | Ayers |

(Continued)

FOREIGN PATENT DOCUMENTS

| | | |
|---|---|---|
| EP | 0032793 A2 | 7/1981 |
| EP | 0147146 A2 | 7/1985 |

(Continued)

OTHER PUBLICATIONS

International Search Report and Written Opinion of International Application No. PCT/IB2009/052990 dated Mar. 2, 2010.
Kamath, et al., "Finishing of Nonwoven Bonded Fabrics," http://web.utk.edu/~mse/Textiles/Finishing%20of%20Nonwovens.htm, updated Apr. 2004, printed Aug. 5, 2008 (11 pages).
"Materials Science & Engineering 554, Nonwovens Science and Technology II," http://web.utk.edu/~mse/Textiles/index.html, Spring 2004, printed Aug. 5, 2008 (2 pages).
GAO, et al., "Thermal Bonding of Nonwoven Fabrics," Educational Research Nonwoven Thermal Bonding, http://www.apparelsearch.com/Education/Research/Nonwoven/2001_Kermit_Duckett/education_research_nonwoven_thermal_bonding.htm, 2001, printed Aug. 4, 2008 (10 pages).

(Continued)

*Primary Examiner* — Audrea Buckley
(74) *Attorney, Agent, or Firm* — Armstrong Teasdale LLP (57) ABSTRACT

Substrates having formulations disposed thereon, wherein the formulations have improved transfer rates from the substrate to skin, are disclosed herein. More particularly, the formulations can be applied to nonwoven, particularly elastomeric substrates, as well as tissue paper, and can be easily and efficiently transferred from the substrate to the skin of a user upon intimate contact thereto. Laminated articles using one or more of the substrates having the formulations disposed thereon are further disclosed.

8 Claims, 3 Drawing Sheets

(56) References Cited

U.S. PATENT DOCUMENTS

| | | |
|---|---|---|
| 4,011,389 A | 3/1977 | Langdon |
| 4,134,838 A | 1/1979 | Hooper et al. |
| 4,137,180 A | 1/1979 | Naik et al. |
| 4,191,609 A | 3/1980 | Trokhan |
| 4,208,459 A | 6/1980 | Becker et al. |
| 4,239,065 A | 12/1980 | Trokhan |
| 4,340,563 A | 7/1982 | Appel et al. |
| 4,347,931 A | 9/1982 | Ginger et al. |
| 4,528,239 A | 7/1985 | Trokhan |
| 4,637,859 A | 1/1987 | Trokhan |
| 4,720,415 A | 1/1988 | Vander Wielen et al. |
| 4,767,547 A | 8/1988 | Straathof et al. |
| 4,788,733 A | 12/1988 | Lerner |
| 4,789,491 A | 12/1988 | Chang et al. |
| 4,812,284 A | 3/1989 | Fleissner |
| 5,169,251 A | 12/1992 | Davis |
| 5,213,881 A | 5/1993 | Timmons et al. |
| 5,364,382 A | 11/1994 | Latimer et al. |
| 5,486,166 A | 1/1996 | Bishop et al. |
| 5,490,846 A | 2/1996 | Ellis et al. |
| 5,539,056 A | 7/1996 | Yang et al. |
| 5,596,052 A | 1/1997 | Resconi et al. |
| 5,607,551 A | 3/1997 | Farrington, Jr. et al. |
| 5,614,202 A | 3/1997 | DeFina |
| 5,639,532 A | 6/1997 | Wells |
| 5,690,918 A | 11/1997 | Jacks et al. |
| 5,869,072 A | 2/1999 | Berry |
| 6,013,270 A * | 1/2000 | Hargraves et al. ........... 424/401 |
| 6,037,281 A | 3/2000 | Mathis et al. |
| 6,180,584 B1 | 1/2001 | Sawan et al. |
| 6,261,580 B1 | 7/2001 | Lehrter et al. |
| 6,274,154 B1 | 8/2001 | Chou |
| 6,383,999 B1 | 5/2002 | Coyle et al. |
| 6,423,328 B2 | 7/2002 | Chou |
| 6,428,794 B1 | 8/2002 | Klofta |
| 6,500,443 B1 | 12/2002 | Otts et al. |
| 6,500,563 B1 | 12/2002 | Datta et al. |
| 6,513,998 B1 | 2/2003 | Barry |
| 6,630,152 B2 | 10/2003 | Chou |
| 6,638,587 B1 | 10/2003 | Wang et al. |
| 6,896,766 B2 * | 5/2005 | Sarbo et al. ................ 162/112 |
| 6,953,582 B2 | 10/2005 | Chou |
| 6,958,103 B2 | 10/2005 | Anderson et al. |
| 6,960,349 B2 | 11/2005 | Shantz et al. |
| 7,147,752 B2 | 12/2006 | Shannon et al. |
| 2002/0006886 A1 | 1/2002 | Beerse et al. |
| 2003/0228351 A1 | 12/2003 | Hasenochrl et al. |
| 2004/0115250 A1 | 6/2004 | Loo et al. |
| 2004/0122382 A1 | 6/2004 | Johnson et al. |
| 2004/0126604 A1 | 7/2004 | Wang et al. |
| 2004/0241201 A1 * | 12/2004 | Wang et al. ................ 424/401 |
| 2005/0079192 A1 | 4/2005 | Simon |
| 2005/0081278 A1 | 4/2005 | Williams |
| 2005/0106201 A1 | 5/2005 | Janssen |
| 2005/0222543 A1 | 10/2005 | Shao |
| 2005/0260147 A1 | 11/2005 | Elliott et al. |
| 2006/0008621 A1 | 1/2006 | Gusky et al. |
| 2006/0070167 A1 | 4/2006 | Eng et al. |
| 2006/0074029 A1 | 4/2006 | Leece |
| 2006/0143767 A1 | 7/2006 | Yang et al. |
| 2007/0244203 A1 | 10/2007 | Raul et al. |
| 2007/0259029 A1 | 11/2007 | McEntire et al. |

FOREIGN PATENT DOCUMENTS

| | | | |
|---|---|---|---|
| EP | 0591609 A1 | 4/1994 | |
| EP | 0617164 A1 | 9/1994 | |
| EP | 0677612 A2 | 10/1995 | |
| EP | 1088540 * | 4/2001 | ............. 424/401 |
| EP | 1125540 A1 | 8/2001 | |
| EP | 1266600 A1 | 12/2002 | |
| EP | 1444970 A1 | 8/2004 | |
| EP | 1454577 A2 | 9/2004 | |
| FR | 2813777 | 3/2002 | |
| WO | 2003022962 A2 | 3/2003 | |
| WO | 2003075879 A2 | 9/2003 | |
| WO | 03105916 A1 | 12/2003 | |
| WO | 2003105916 A1 | 12/2003 | |
| WO | 2004043179 A2 | 5/2004 | |
| WO | 2004043235 A2 | 5/2004 | |
| WO | 2004060432 A1 | 7/2004 | |
| WO | 2004108036 A1 | 12/2004 | |
| WO | 2006110271 | 10/2006 | |
| WO | 2007018822 A1 | 2/2007 | |
| WO | 2007064343 A2 | 6/2007 | |

OTHER PUBLICATIONS

Quack, R., et al., "Calender Processes in the Nonwoven Industry," International Nonwovens Technical Conference, INTC 2001, Sep. 5-7, 2001, 15p.

Scruggs, J., "A brief overview of the evolution of propylene fiber processes," Propylene Technology Conference, Aug. 31-Sep. 1, 1994, 10 p.

Smith, P., "Nonwoven Fabric Machinery," Textile Hroizons, Feb./Mar. 1992, vol. 12, Issue 2, p. 34-35.

Reddy, et al., "Stability Testing of O/W Emulsions Through Dielectric Constant—I," Cosmetics & Toiletries, vol. 99 (10), Oct. 1984, p. 67-72.

International Search Report and Written Opinion of International Application No. PCT/IB2009/050240, dated Sep. 24, 2009.

Product information for ABIL WE 09; EVONIK Industries, 2008.

International Search Report and Written Opinion of International Application No. PCT/IB2009/052989, dated Feb. 26, 2010.

Non-final Office Action regarding U.S. Appl. No. 12/022,328, dated Jun. 28, 2011.

Final Office Action regarding U.S. Appl. No. 12/022,328, dated Dec. 6, 2011.

Non-final Office Action regarding U.S. Appl. No. 12/172,039, dated Dec. 8, 2011.

Patent Examination Report No. 2 issued in Australian Patent Application No. 2009269611 (Dec. 16, 2013)(3 pages).

European Search Report for Application No. 09794091 dated Jul. 4, 2013; 6 pages.

Office Action for Russian Application No. 2011104725/15 dated Nov. 23, 2012; 6 pages.

Patent Examination Report No. 1 for Patent Application No. 2009269612 dated Aug. 20, 2013; 5 pages.

Office Action for Russian Application No. 2011104727/15 dated Dec. 14, 2012; 4 pages.

Lewis, Sr. Richard J., "Hawley's Condensed Chemical Dictionary," Wiley-Interscience, p. 854 (2007).

Office action issued for U.S. Appl. No. 12/022,328 (dated Dec. 19, 2013).

Supplementary European Search Report for EP 09794090, dated Apr. 8, 2013, 6 pages.

Patent Examination Report No. 2 issued in Australian Patent Application No. 2009269611 (dated Dec. 16, 2013)(3 pages).

* cited by examiner

FIG. 3A ially, it would be advantageous if the lotions could be applied to laminated articles such as gloves or socks that can be donned and conformed to the surface of the user's skin to provide health and hygiene benefits.

SUBSTRATES HAVING FORMULATIONS WITH IMPROVED TRANSFERABILITY

BACKGROUND OF THE DISCLOSURE

The present disclosure relates generally to substrates having formulations disposed thereon, wherein the formulations have improved transferability from the substrates to the skin of the user. More particularly, the formulations can be applied on nonwoven or elastomeric substrates to be easily transferred to the skin. In one embodiment, the formulation has a transfer rate of at least about 25% or greater when the viscosity of the formulation is 8,000 cP or greater as defined herein. In another embodiment, a tissue paper product can be prepared having a formulation applied thereon that can easily and efficiently be applied to the user's skin.

Consumers have conventionally relied upon various kinds of formulations or compositions for health and/or hygiene benefits. To deliver these benefits, a wide variety of chemistries are often used within a single formulation. One of the more prevalent delivery forms, emulsions such as lotions and creams, are particularly useful as they combine high levels of both water and oily substances to deposit on the skin. More particularly, lotions include skin benefit components such as humectants, occlusive agents, emollients, and emulsifiers.

Humectants are hygroscopic agents that are typically used as moisturizers. Furthermore, occlusive agents help improve the overall moisture content of the skin by retarding the evaporation of water from the skin's surface. By blocking the evaporative loss of water, occlusive agents increase the water content of skin.

Lotions additionally rely on emollients to lubricate, sooth, and soften the skin surface. Emollients are generally oily or waxy ingredients that have a major impact on the aesthetics of the finished formulations and on the separation of the water and oil within a lotion emulsion. They also significantly influence the spreading characteristics and overall skin feel of the lotion.

One major problem with conventionally used components in lotion formulations is that only a small portion of the formulation actually transfers to the skin via intimate contact with a nonwoven or other substrate, and thus, the remaining formulation is lost to the consumer. For the consumer, this means a product that lacks efficacy and overall benefit. Additionally, this problem is also extremely significant and costly to the manufacturers of the products using the formulations. First, to remedy the low transfer of formulation, companies have to either increase levels of the actives in the formulations or the overall formulation saturation level on the substrates and/or article. Actives are generally extremely expensive and increasing their levels will greatly increase the costs of producing the products. In addition, increasing active levels can increase the risk of skin irritation, which ultimately creates a more stringent testing protocol. Alternatively, increasing the overall formulation saturation level to compensate for the low transfer efficiency has resulted in high formulation load that increases costs and has the potential to destabilize the basesheet and/or cause delamination of the article.

As such, there is a significant need for formulations including oily substances and other skin benefit actives that can be applied to the surface of nonwoven, elastomeric, and/or tissue paper substrates that will provide desired skin health benefits and have good aesthetics to the user while also having efficient high transfer to the user's skin. Additionally, it would be advantageous if the lotions could be applied to laminated articles such as gloves or socks that can be donned and conformed to the surface of the user's skin to provide health and hygiene benefits.

BRIEF DESCRIPTION OF THE DISCLOSURE

It has been found that formulations can be produced and applied to substrates and articles for improving skin health that have an improved transfer rate. Particularly, these formulations include components that can improve skin feel and overall aesthetics and can be efficiently and effectively transferred from the substrate to the user's skin via intimate contact of the substrate with the skin. In one embodiment, particularly preferred substrates for use with the formulation include nonwoven substrates and elastomeric substrates. In another embodiment, the formulation is applied to tissue paper to be transferred to skin. Generally, the formulation can include at least one cosmetic carrier for improving skin health and hygiene when applied to the skin.

Additionally, the formulation can be applied to the inner surface of a laminated article capable of conforming to the user's skin when donned. In one preferred embodiment, the laminated article is a glove.

Accordingly, the present disclosure is directed to an elastomeric substrate comprising a formulation. The formulation comprises at least one cosmetic carrier and has greater than 5% (by weight formulation) water. The formulation further has a transfer rate of at least 25% when the viscosity of the formulation is 8,000 cP or greater.

The present disclosure is further directed to a laminated article comprising an elastomeric substrate and a second substrate. The elastomeric substrate comprises a formulation including at least one cosmetic carrier and having greater than 5% (by weight formulation) water. The formulation further has a transfer rate of at least 25% when the viscosity of the formulation is 8,000 cP or greater.

The present disclosure is further directed to a method of preparing a tissue paper. The method includes forming a tissue web; and applying a formulation to the outer surface of the tissue web in a single processing step. The formulation includes at least one cosmetic carrier and has greater than 5% (by weight formulation) water. The formulation further has a transfer rate of at least 25% when the viscosity of the formulation is 8,000 cP or greater.

Other objects and features will be in part apparent and in part pointed out hereinafter.

DETAILED DESCRIPTION OF THE DISCLOSURE

The present disclosure is directed to various substrates having a formulation deposited thereon for providing skin health and/or hygiene benefits, wherein the formulation has an improved transfer rate from the substrate to skin. Generally, the substrate can be a nonwoven, elastomeric or tissue paper substrate. More particularly, the formulation includes greater than 5% (by weight formulation) water, and preferably, is an emulsion formulation. The formulation further includes at least one cosmetic carrier that can provide one or more skin benefits to the user and can provide for more efficient and effective transfer of the formulation from the substrate to skin.

Additionally, the present disclosure is directed to laminated articles made from the substrates. Particularly, the laminated articles have at least a first outer substrate and a second inner substrate. At least one or both of the first and second substrates may be an elastomeric substrates.

Representative Substrates for Use with the Formulations of the Present Disclosure In one embodiment, the substrate is an elastomeric substrate. Elastomeric substrates are particularly useful when the substrate is to be used in a laminated article such as a glove or sock, as it is oftentimes desirable for the glove or sock to be able to stretch to provide for easier glove/sock donning. The elastomeric substrate may be formed from a natural or a synthetic latex as well as a dissolved or hot melt extrusion of an elastomeric polymer, such as a thermoplastic elastomeric polyolefin polymer. For instance, the elastomeric substrate may be formed of a natural or synthetic rubber, a nitrile rubber, a nitrile butadiene rubber, a polyisoprene, a polychloroprene, a polyurethane, a neoprene, a homopolymer of a conjugated diene, a copolymer of a least two conjugated dienes, a copolymer of at least one conjugated diene and at least one vinyl monomer, styrene block copolymers, or any other suitable combinations thereof. Examples of suitable synthetic rubbers can also include acrylic diene block co-polymers, acrylic rubber, butyl rubber, EPDM rubber, polybutadiene, chlorosulfonated polyethylene rubber, and fluororubber.

The elastomeric substrates (also referred to herein as films) can be formed by mixing the components together, heating and then extruding the components into a monolayer or multi-layer substrate using any one of a variety of elastomeric film-producing processes known to those of ordinary skill in the film processing art. Such film-making processes include, for example, cast embossed, chill and flat cast, and blown film processes.

In one particularly preferred embodiment, the elastomeric substrate is a nonwoven substrate. When a nonwoven substrate is used with the formulation, commercially available thermoplastic polymeric materials can be advantageously employed in making the fibers or filaments from which the substrate is formed. As used herein, the term "polymer" shall include, but is not limited to, homopolymer, copolymers, such as for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymer material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers thereof.

Alternatively, or in addition to the polymeric materials above, the nonwoven substrates can be prepared from cellulosic fibers. Numerous cellulosic fibers, such as, for example, wood pulp fibers or staple fibers can be used in the nonwoven substrates. Suitable commercially available cellulosic fibers for use in the nonwoven substrates can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

Nonwoven substrates can be formed by a variety of known forming processes, including airlaying, meltblowing, spunbonding, or bonded carded web formation processes. "Airlaid" refers to a porous web formed by dispersing fibers in a moving air stream prior to collecting the fibers on a forming surface. The collected fibers are then typically bonded to one another using, for example, hot air or a spray adhesive. Suitable examples of airlaid webs can be found in U.S. Pat. No. 5,486,166 to Bishop, et al., U.S. Pat. No. 6,960,349, issued to Shantz, et al. (Nov. 1, 2005), and U.S. Publication No. 2006/0008621 to Gusky, et al., all incorporated by reference to the extent that they are consistent herewith.

The fibrous nonwoven substrate material may also comprise meltblown materials. "Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al. , U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns.

"Bonded-carded web" refers to a web made from staple fibers sent through a combing or carding unit, which separates or breaks apart and aligns the fibers to form a nonwoven web. For example, the web may be a powder bonded carded web, an infrared bonded carded web, or a through-air bonded carded web. Examples of such materials may be found in U.S. Pat. No. 5,490,846 to Ellis et al.; U.S. Pat. No. 5,364,382 to Latimer; and U.S. Pat. No. 6,958,103 to Anderson, et al.

As noted above, these substrates can be used alone or can be combined to form a laminated article having at least a first substrate and a second substrate. Particularly, at least one of the first and second substrate is an elastomeric substrate.

Figure 1:
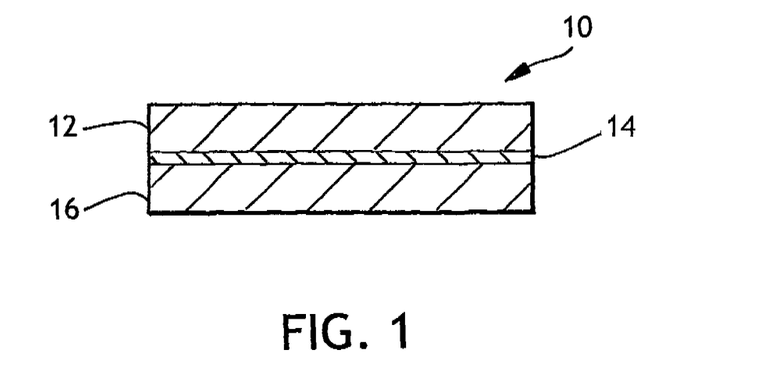
FIG. 1 depicts one embodiment of a laminated article of the present disclosure.

One particularly preferred laminated article of the present disclosure will generally have 3 layers: a water-impermeable substrate, such as a film, sandwiched between two fibrous substrates, such as the nonwoven substrates described above. An example of such a laminated article 10 is depicted in FIG. 1, which representatively illustrates a water-impermeable substrate 14 attached to an outer fibrous substrate 12 and an inner fibrous substrate 16. The material for the outer fibrous substrate 12 may be any nonwoven substrate material described above that provides for a cloth-like appearance (as opposed to, for example, a smooth or rubbery appearance as in neoprene rubber glove). The material for the inner fibrous substrate 16 may be any material that is fibrous in nature, such as the above-described nonwoven substrates.

In one embodiment, the inner fibrous substrate should possess an uneven, undulating surface to help contain the formulation applied to the surface of the inner fibrous substrate 16. The undulations (rugosity) of this inner substrate material can be achieved or enhanced by attaching the inner fibrous substrate 16 to the water-impermeable substrate 14 at discrete points or locations (e.g., by thermally point bonding the substrates together, as is discussed in more detail below) while the water-impermeable substrate 14 is in a stretched condition. When the water-impermeable substrate 14 (and, therefore, the resulting laminate article) is allowed to relax, the inner fibrous substrate 16 is gathered to produce undulations in the inner fibrous layer. Of course, both the inner fibrous substrate 16 and the outer fibrous substrate 12 are gathered in this way if they are attached to the water-impermeable substrate 14 at discrete points or locations while the water-impermeable substrate 14 is in a stretched condition (and then allowed to relax).

The inner and outer fibrous nonwoven substrates may be the same or may be different. Generally the water-impermeable substrate 14 is an elastomeric substrate, with the resulting laminated article 10 able to stretch and conform to a hand, foot, extremity, or other body region to which the article is applied.

As noted above, the water-impermeable substrate 14 is typically the elastomeric substrate as described above. In addition, however, additional layers of water-impermeable substrates formed of any other film-type substrate that can be suitably bonded or attached to inner and outer fibrous substrate layers 12 and 16 respectively to yield a laminated article 10 having the performance characteristics and features described herein can also be included within the article. In addition to the polyolefin film-type material, the water-impermeable substrate 14 can also include a filler. As used herein, a "filler" is meant to include particulates and other forms of materials which can be added to the film polymer (e.g., elastomeric) extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present disclosure provided that they do not interfere with the film formation process, or the ability of the film layer to function in accordance with the teachings of the present disclosure. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles.

As mentioned herein, water-impermeable substrate 14 may be formed using any one of the conventional processes known to those familiar with elastomeric and/or film formation. The polyolefin polymer and any optional ingredients (e.g., filler) are mixed in and then heated and extruded into a film.

The water-impermeable substrate of the present disclosure may be described as a mono-layer film or, as other types, such as multi-layer films, provided the forming technique is compatible with films described herein.

Typically the water-impermeable substrate 14 will be attached to the outer fibrous substrate 12 and inner fibrous substrate 16 by thermally bonding the three layers together at discrete points (see, e.g., discussion in preceding paragraph as well as U.S. Pat. No. 6,037,281, entitled "Cloth-Like, Liquid-Impervious, Breathable Composite Barrier Fabric," to Mathis, et al.). As noted above, the two fibrous substrates may be bonded or attached to the water-impermeable substrate at discrete locations while the water-impermeable substrate is in a stretched condition, thereby producing undulations when the resulting laminated article is in a relaxed condition. Other known means for bonding and laminating the water-impermeable substrate 14 to fibrous substrates 12, 16 may be used, provided the resulting laminated article 10 has the required properties described herein. For example, the three substrates may be adhesively bonded to one another.

While described herein as using a water-impermeable substrate, it should be understood that, in some embodiments, the substrates and laminated articles can be made from layers that are not water-impermeable without departing from the scope of the present disclosure.

Other additives and ingredients may be added to the water-impermeable substrate 14 provided they do not significantly interfere with the ability of the substrate to function in accordance with the teachings of the present disclosure. Such additives and ingredients can include, for example, antioxidants, stabilizers, and pigments.

While described herein as having three substrate layers, it should be recognized by one skilled in the art that the laminated article can have only two substrates bonded together or can have more than three substrate layers, such as four substrates, five substrates or even six or more substrates without departing from the present disclosure. In certain embodiments, the presence of a water-impermeable substrate layer is not required.

Representative Laminated Articles

One or more laminated articles, such as those described above, must be configured into the form of a glove, mitten, sock, sleeve, patch, or other article designed to be fitted to a part of the user's body. Generally the article will be made by cutting at least first and second substrates into appropriate pieces such that the pieces, when attached to one another, form an article having an interior volume into which a portion of a user's body may be inserted.

Figure 2:
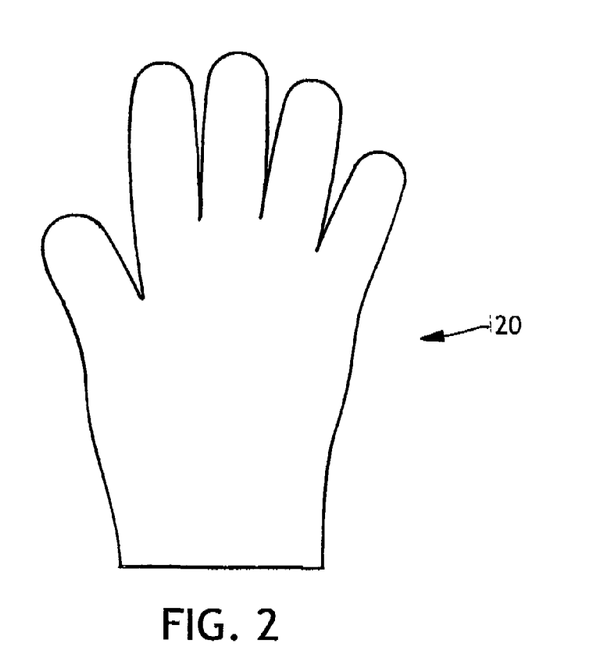
FIG. 2 depicts one embodiment of a substrate for use in a laminated article cut so that the substrate's perimeter defines the shape of a user's hand.
Figure 2A:
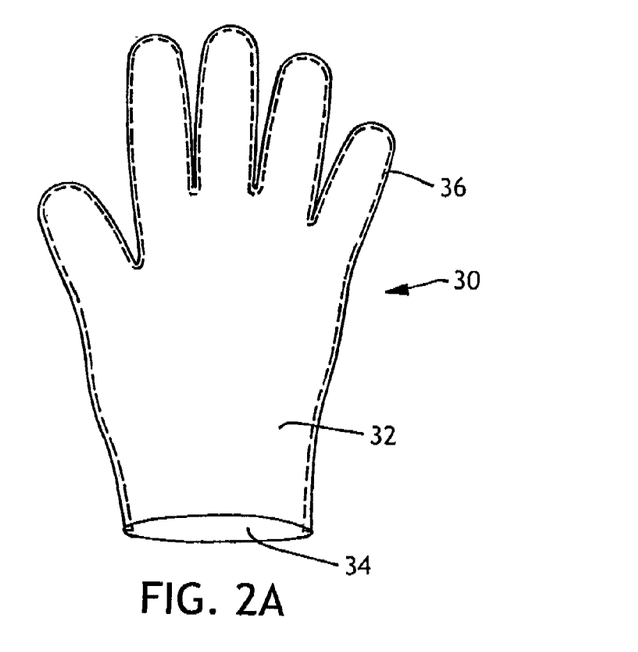
FIG. 2A depicts a laminated article using the substrate of FIG. 2.

FIG. 2 representatively depicts a first substrate 20 cut so that the piece (or substrate) defines a perimeter in the shape of a human hand. FIG. 2A representatively depicts an article 30 comprising a first substrate 32 attached to a second substrate 34 at a location proximate to the perimeters of these two substrates. In this representative illustration, the two substrates are attached to one another mechanically by sewing the pieces together at a location proximate to the perimeters of the two substrates. The resulting article was then inverted so that the seam 36 formed by sewing the substrates together is on the interior of the article. Of course the finished article need not be inverted; the seam can remain on the exterior of the article. Note, too, that the individual substrates need not be joined in a way that produces a seam. The edges of the individual substrates may be butted together, and then, for example, joined and/or welded together using a solvent.

Alternatively, the individual substrates may be butted together, and another material, such as an adhesive or an adhesive tape, used to join the substrates together.

Individual substrates may be cut into a variety of shapes and sizes. Rather than the glove depicted in FIGS. 2 and 2A, the substrates may be cut so that the resulting article is in the shape of a tube, sleeve, mitten, sock, or the like. Any shape is possible, so long as the resulting article defines an interior volume into which a user may insert a portion of his or her body (e.g., a finger, toe, hand, foot, wrist, forearm, etc.) such that a formulation, as described herein below, applied to the interior surface of the article may be transferred to skin or tissue in contact with the interior surface of the article.

The individual substrates need not be sewn together. The individual substrates may also be joined ultrasonically, thermally, adhesively, cohesively, using tape, by fusing the substrates together (e.g., by using an appropriate solvent), by welding the substrates together, or by other approaches. So long as the individual substrates remain attached or connected during normal use of the article, and attachment or connection is such that the formulation on the interior surface of the article is contained within the article (i.e., there is minimal or no leakage of the formulation), any connection or attachment may be used.

Alternatively, a substrate could be prepared in the form of a rectangle, oval or other shape. An adhesive capable of adhering to skin could then be applied to all or part of the perimeter of the shape such that the article could be releasably adhered to skin. The formulation to be transferred to skin could then be coated or deposited on the surface of the article that will contact skin or tissue.

Figure 3:
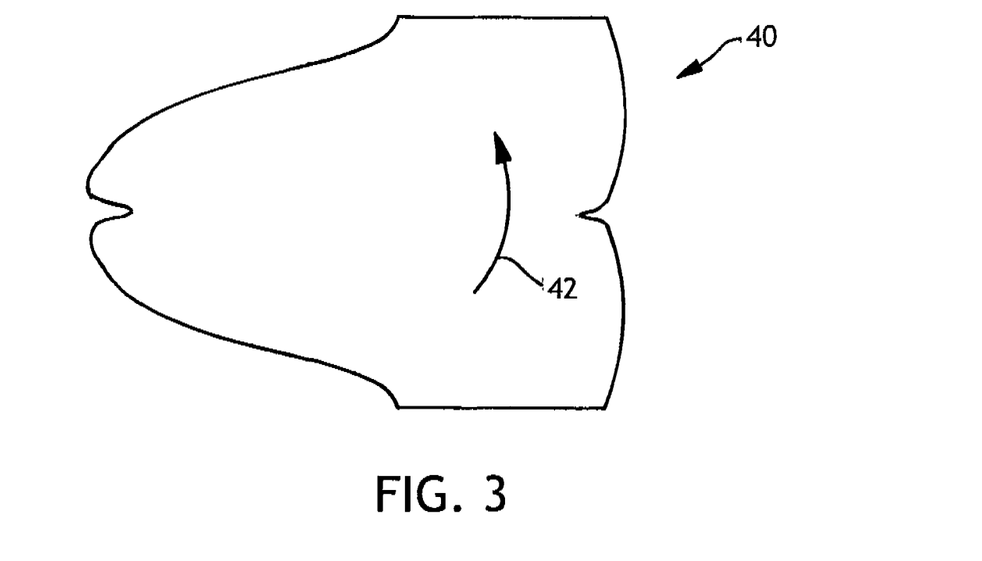
FIG. 3 depicts a second embodiment of a substrate for use in a laminated article cut so as to form a foot-configured laminated article of the present disclosure.
Figure 3A:
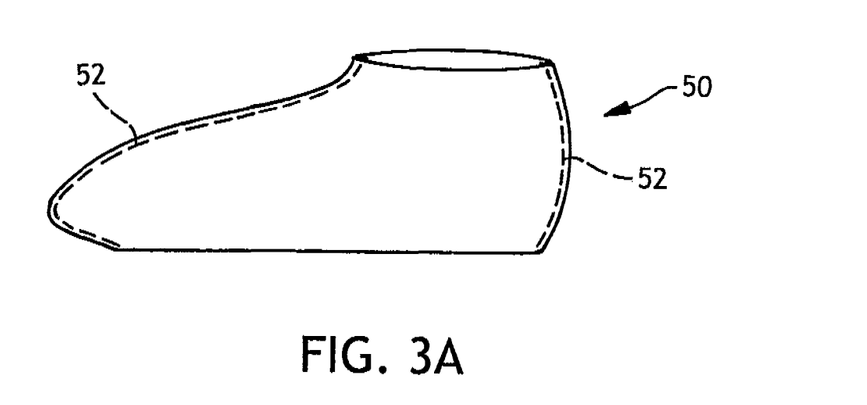
FIG. 3A depicts a laminated article using the substrate of FIG. 3.

Note, too, that an article may be formed from a single piece of a first substrate. FIG. 3 representatively illustrates a first substrate 40 that has been cut in a way that a foot-shaped article may be formed by folding the substrate back on itself (as shown by arrow 42; the bottom half of the shape is folded upward, and on top of, the top half of the shape). FIG. 3A representatively illustrates such a foot-shape article 50 and the resulting seams 52 formed when the substrate 40 (from FIG. 3) is folded back, and attached to, itself. In this representative embodiment, the foot-shape article was inverted after the substrate was attached to itself so that the seams were on the inside of the article. As with two (or more) substrates that may be joined together to form an article of the present disclosure, a single substrate may be joined to itself using any of the approaches discussed above.

Tissue Paper Substrates for Use With the Formulations

Alternatively, the formulation may be applied to a tissue paper. As used herein, the terms "tissue paper web," "paper web," "web," and "paper sheet" all refer to sheets of paper made by a process comprising the steps of forming an aqueous papermaking furnish, depositing this furnish on a foraminous surface, such as a Fourdrinier wire, and removing the water from the furnish as by gravity or vacuum-assisted drainage, with or without pressing, and by evaporation.

As used herein, an aqueous papermaking furnish is an aqueous slurry of papermaking fibers and the chemicals described hereinafter.

The first step in a particularly preferred process for making the treated tissue paper of this disclosure is the forming of an aqueous papermaking furnish. The furnish includes papermaking fibers (hereinafter sometimes referred to as wood pulp) and any optional components for providing aesthetic and functional properties of the tissue paper as desired. For example, in one embodiment, the furnish can include at least one wet strength resin. More particularly, wet strength resins can include water-soluble, cationic materials as known in the art and further described in U.S. Pat. No. 6,261,580, issued to Lehrter, et al. (Jul. 17, 2001).

The wood pulp for use in the furnish can be any type and variety of wood pulp as known in the art. Wood pulps useful herein include chemical pulps such as Kraft and sulfite pulps, as well as mechanical pulps, including for example, ground wood, thermomechanical pulps, and chemically modified thermomechanical pulps (CTMP). Pulps derived from both deciduous and coniferous trees can also be used. Also applicable to the present disclosure include fibers derived from recycled paper, which may contain any or all of the above categories as well as other non-fibrous materials such as fillers and adhesives used to facilitate the original papermaking. Preferably, the papermaking fibers used in this disclosure comprise Kraft pulp derived from northern softwoods, Kraft pulps derived from eucalyptus, and mixtures thereof. Other cellulosic fibrous pulps, such as cotton linters, bagasse, rayon, and the like can be used.

Other chemicals commonly used in papermaking can be added to the papermaking furnish so long as they do not significantly and adversely affect the transferability of the formulation from the tissue paper end-product.

For example, surfactants may be used to treat the tissue paper webs of the present disclosure. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as Crodesta™ SL-40, which is available from Croda, Inc. (New York, N.Y.); alkylglycoside ethers as described in U.S. Pat. No. 4,011,389, issued to W. K. Langdon, et al. on Mar. 8, 1977; and alkylpolyethoxylated esters such as Pegosperse™ 200 ML available from Glyco Chemicals, Inc. (Greenwich, Conn.) and IGEPAL RC-520 available from Rhone Poulenc Corporation (Cranbury, N.J.).

Other types of chemicals which may be added include dry strength additives to increase the tensile strength of the tissue webs. Examples of dry strength additives include carboxymethyl cellulose, and cationic polymers from the ACCO chemical family such as ACCO 771 and ACCO 514, with carboxymethyl cellulose being preferred. This material is available commercially from the Hercules Company of Wilmington, Del. under the tradename HERCULES® CMC. The level of dry strength additive, if used, is preferably from about 0.01% to about 1.0%, by weight, based on the dry fiber weight of the tissue paper.

The above listings of additional chemical additives are intended to be merely exemplary in nature, and are not meant to limit the scope of the present disclosure.

The papermaking furnish can be readily formed or prepared by mixing techniques and equipment well known to those skilled in the papermaking art. Typically, an aqueous slurry of papermaking fibers (and any optional components) is added to a wet end of the papermaking machine at some suitable point ahead of the Fourdrinier wire or sheet forming stage.

The second step in the process is the depositing of the papermaking furnish on a foraminous surface to form a tissue web and the third is the removing of the water from the web so deposited. Techniques and equipment which can be used to accomplish these two processing steps will be readily apparent to those skilled in the papermaking art.

The present disclosure is applicable to making tissue paper in general, including but not limited to conventionally felt-pressed tissue paper; pattern densified tissue paper such as exemplified U.S. Pat. No. 3,301,746, Sanford and Sisson, issued Jan. 31, 1967; and high bulk, uncompacted tissue paper such as exemplified by U.S. Pat. No. 3,812,000, Salvucci, Jr., issued May 21, 1974. The tissue paper may be of a homogenous or multilayered construction; and tissue paper products made therefrom may be of a single-ply or multi-ply construction. The tissue paper preferably has a basis weight of between 10 g/m² and about 65 g/m², and density of about 0.60 g/cc or less. Preferably, the basis weight will be below about 35 g/m² (or even less); and the density will be about 0.30 g/cc (or even less). Most preferably, the density will be between about 0.04 g/cc and about 0.20 g/cc.

Conventionally pressed tissue paper and methods for making such paper are known in the art. Such paper is typically made by depositing papermaking furnish on a foraminous forming wire. This forming wire is often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided in a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a stream drum apparatus known in the art as a Yankee dryer. Pressure can be developed at the Yankee dryer by mechanical means such as an opposing cylindrical drum pressing against the web. Multiple Yankee dryer drums may be employed, whereby additional pressing is optionally incurred between the drums. The tissue paper structures which are formed are referred to hereinafter as conventional, pressed, tissue paper structures. Such sheets are considered to be compacted since the web is subjected to substantial mechanical compressional forces while the fibers are moist and are then dried (and optionally creped) while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones may be discretely spaced within the high bulk field or may be interconnected, either fully or partially, within the high bulk field. Preferred processes for making pattern densified tissue webs are disclosed in U.S. Pat. No. 6,896,766, issued to Sarbo, et al. on May 24, 2005; U.S. Pat. No. 3,301,746, issued to Sanford and Sisson on Jan. 31, 1967, U.S. Pat. No. 3,974,025, issued to Peter G. Ayers on Aug. 10, 1976, and U.S. Pat. No. 4,191,609, issued to Paul D. Trokhan on Mar. 4, 1980, and U.S. Pat. No. 4,637,859, issued to Paul D. Trokhan on Jan. 20, 1987; the disclosures of each of which are incorporated herein by reference to the extent that they are consistent herewith.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further densified by application of fluid pressure, such as with a vacuum type device or a blow-through dryer, or by mechanically pressing against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones may be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface includes densified knuckles having a relative density of at least 125% of the density of the high bulk field.

The array of supports is preferably an imprinting carrier fabric having a patterned displacement of knuckles which operate as the array of supports which facilitate the formation of the densified zones upon application of pressure. The pattern of knuckles constitutes the array of supports previously referred to. Imprinting carrier fabrics are disclosed in U.S. Pat. No. 6,896,766, issued to Sarbo, et al. on May 24, 2005; U.S. Pat. No. 3,301,746, Sanford and Sisson, issued Jan. 31, 1967, U.S. Pat. No. 3,821,068, Salvucci, Jr. et al., issued May 21, 1974, U.S. Pat. No. 3,974,025, Ayers, issued Aug. 10, 1976, U.S. Pat. No. 3,573,164, Friedberg et al., issued Mar. 30, 1971, U.S. Pat. No. 3,473,576, Amneus, issued Oct. 21, 1969, U.S. Pat. No. 4,239,065, Trokhan, issued Dec. 16, 1980, and U.S. Pat. No. 4,528,239, Trokhan, issued Jul. 9, 1985, the disclosures of each of which are incorporated herein by reference to the extent that they are consistent herewith.

Preferably, the furnish is first formed into a wet web on a foraminous forming carrier, such as a Fourdrinier wire. The web is dewatered and transferred to an imprinting fabric. The furnish may alternately be initially deposited on a foraminous supporting carrier which also operates as an imprinting fabric. Once formed, the wet web is dewatered and, preferably, thermally predried to a selected fiber consistency of between about 40% and about 80%. Dewatering can be performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll which supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure may be applied to induce impression of densified zones during initial dewatering, in a separate, subsequent process stage, or a combination thereof.

Uncompacted, nonpattern-densified tissue paper structures are described in U.S. Pat. No. 7,147,752 issued to Shannon, et al. on Dec. 12, 2006; U.S. Pat. No. 3,812,000 issued to Joseph L. Salvucci, Jr. and Peter N. Yiannos on May 21, 1974 and U.S. Pat. No. 4,208,459, issued to Henry E. Becker, Albert L. McConnell, and Richard Schutte on Jun. 17, 1980, both of which are incorporated herein by reference to the extent that they are consistent herewith. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least 80%, and creping the web. Water is removed from the web by vacuum dewatering and thermal drying. The resulting structure is a soft but weak high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25-50%, transferring the web to a thermal dryer such as a Yankee and creping the web. Overall, water is removed from the web by vacuum, mechanical pressing and thermal means. The resulting structure is strong and generally of singular density, but very low in bulk, absorbency and in softness.

While the characteristics of the creped paper webs, particularly when the creping process is preceded by methods of pattern densification, are preferred for practicing the present disclosure, uncreped tissue paper is also a satisfactory substitute and the practice of the present disclosure using uncreped tissue paper is specifically incorporated within the scope of the present disclosure. "Uncreped tissue paper," a term as used herein, refers to tissue paper which is non-compressively dried, most preferably by throughdrying. The techniques to produce such uncreped tissue are taught in the prior art. For example, Wendt, et. al. in European Patent Application 0 677 612A2, published Oct. 18, 1995 and Farrington, Jr., et al. in U.S. Pat. No. 5,607,551, issued Mar. 4, 1997, the disclosure of each being incorporated herein by reference to the extent that they are consistent herewith, teach a method of making soft tissue products without creping. In another case, Hyland, et. al. in European Patent Application 0 617 164 A1, published Sep. 28, 1994 and incorporated herein by reference, teach a method of making smooth uncreped throughdried sheets.

Representative Formulations for Use with the Substrates and Laminated Articles Made Therefrom As noted above, the formulations for use with the substrates and laminated articles of the present disclosure are capable of improving the user's skin health and hygiene and are easily and efficiently transferred from the substrate and/or article to the user's skin.

Generally, the formulations of the present disclosure include at least one cosmetic carrier. As used herein, the term "cosmetic carrier" refers to both hydrophilic and hydrophobic carriers that do not interfere with the mechanical properties of the substrates and/or laminated articles made therefrom. Suitable hydrophilic carriers include, but are not limited to, propylene glycol, butylene glycol, dipropylene glycol, glycerin, glycereth-18 ethylhexanoate, glycereth-18, betaine, diglycerin, glycol, inositol, meadowfoamamidopropyl betaine, ethyl alcohol, isopropyl alcohol, polyethylene glycol with varied molecular weights, sorbitol, xylitol, urea, tripropylene glycol, sodium PCA, glycereth-7 glycolate, diglycereth-7 malate, 2,3-butanediol, propanediol, xylose, almond oil PEG-6 esters, apricot kernel oil PEG-6 esters, argan oil PEG-8 esters, argan oil polyglyceryl-6 esters. Suitable hydrophobic substances include, but are not limited to, PEG-3 dimethicone, PEG/PPG-20/23 dimethicone;, PEG-8 dimethicone, cyclomethicone, dimethcione, cetyl dimethicone, caprylyl methicone, ethyl trisiloxane, trimethylsiloxyamodimethicone, stearyl dimethicone, silicones with polypropylene glycol functionality such as PPG-12 dimethicone, silicones with polyethylene glycol functionality such as PEG-8 trisiloxane, PEG-10 dimethicone and silicones which combine both functionalities in varying ratios such as PEG/PPG-5/3 trisiloxane, PEG/PPG-8/26 dimethicone, PEG/PPG-20/15 dimethicone, bis-PEG-4 dimethicone, bis-PEG-12 dimethicone, bis-PEG/PPG-14/14 dimethicone, bis-PEG/PPG-18/6 dimethicone, bis-PEG/PPG-20/20 dimethicone, butylene glycol behenate, butylene glycol diisononanoate, butylene glycol laurate, butylene glycol myristate, butylene glycol oleate, butylene glycol palmitate, butylene glycol stearate, butyl isostearate, butyl myristate, butyloctyl behenate, butyloctyl benzoate, butyloctyl cetearate, butyloctyl palmitate, butyl oleate, butyl stearate C14-15 alcohols, C18-28 alkyl acetate, C12-15 alkyl benzoate, C16-17 alkyl benzoate, C30-45 alkyl cetearyl dimethicone crosspolymer, C32 alkyl dimethicone, C30-45 alkyl dimethicone/polycyclohexene oxide crosspolymer, C12-13 alkyl ethylhexanoate, C12-15 alkyl ethylhexanoate, C14-18 alkyl ethylhexanoate, C12-13 alkyl lactate, C12-15 alkyl lactate, C20-24 alkyl methicone, C24-28 alkyl methicone, calodendrum capense nut oil, calophyllum tacamahaca seed oil, cetearyl dimethicone/vinyl dimethicone crosspolymer, cetearyl ethylhexanoate, cetearyl isononanoate, cetearyl nonanoate, cetearyl palmitate, cetrimonium laureth-12 succinate, cetyl acetate, cetyl caprylate, cetyl C12-15 pareth-8 carboxylate, cetyl dimethicone, cetyl dimethicone/bis-vinyldimethicone crosspolymer, cetyl dimethyloctanoate, cetyl esters, cetyl ethylhexanoate, cetyl glyceryl ether, cetyl glycol, cetyl glycol isostearate, cetyl isononanoate, cetyl lactate, cetyl laurate, cetyl oleate, cetyloxy dimethicone, C12-15 pareth-3 benzoate, C 12-15 pareth-9 hydrogenated tallowate, C11-15 pareth-3 oleate, C 12-15 pareth-12 oleate, C 11-15 pareth-3 stearate, C11-15 pareth-12 stearate, dibutyl adipate, dibutyldecyl IPDI, dibutyloctyl IPDI, dibutyloctyl malate, dibutyloctyl sebacate, dibutyl sebacate, Ddi-C12-15 alkyl adipate, di-C12-15 alkyl fumarate, di-C12-13 alkyl malate, di-C12-15 alkyl maleate, di-C12-13 alkyl tartrate, -C14-15 alkyl tartrate, dicaprylyl carbonate, dicaprylyl ether, dicaprylyl maleate, dicetyl adipate, dicocoyl pentaerythrityl distearyl citrate, diethyl adipate, isobutyl myristate, isobutyl palmitate, isobutyl pelargonate, isobutyl stearate, isobutyl tallowate, isocetyl alcohol, isocetyl ethylhexanoate, isocetyl isodecanoate, isocetyl isostearate, isocetyl laurate, isocetyl linoleoyl stearate, isocetyl palmitate, isocetyl stearate, lanolin, lanolin oil, lanolin wax, lauryl lactate, neopentyl glycol diheptanoate, neopentyl glycol diisononanoate, neopentyl glycol dilaurate, octyldodecyl ethylhexanoate, octyldodecyl lactate, octyldodecyl neodecanoate, octyldodecyl neopentanoate, PPG-3 benzyl ether myristate, PPG-1 -ceteth-1, PPG- 1 -ceteth-5, PPG-1-ceteth-10, PPG-1-ceteth-20, sunflower oil, safflower oil, mineral oil and jojoba oil diisoamyl malate, diethylhexyl malate, dibutyloctyl malate, dimethyl capramide, diethylhexyl 2,6 napthalate, N,N-dimethyldesamide, diisopropyl adipate, phenethyl benzoate, octocrylene, PEG-7 methyl ester, and combinations thereof Particularly preferred cosmetic carriers include silicone-containing compounds, esters, amides, and ethers. Other suitable cosmetic carriers could be utilized and are listed in the CTFA Ingredient Dictionary (2007). The selection of suitable cosmetic carriers will vary depending on the substrate that is chosen and must be chosen so as to ensure that the transfer properties of the substrate are maintained.

Suitable silicon-containing compounds include silicone derivatives such as, for example, dimethicone; cetyl dimethicone; PEG/PPG-8/26 dimethicone; PEG/PPG-20/23 dimethicone; PEG/PPG-20/15 dimethicone; PEG-10 dimethicone; PPG-12 dimethicone; caprylyl methicone; ethyl trisiloxane; PEG-8 trisiloxane; PEG/PPG-5/3 trisiloxane; trimethylsiloxyamodimethicone; stearyl dimethicone; and combinations thereof.

Suitable esters, ethers, and glycols for use as the cosmetic carrier include PPG-3 benzyl ether myristate; PEG-7 methyl ester; propylene glycol; and combinations thereof.

Typically, when the cosmetic carrier includes a silicone derivative or ester, the cosmetic carrier includes from about 10% to about 95% by weight silicone derivative, ester, ether, or glycol. More suitably, the cosmetic carrier includes from about 50% to about 100% by weight silicon derivative, ester, ether, or glycol, and even more suitably, from about 75% to about 100% by weight silicone derivative, ester, ether, or glycol.

The amount of cosmetic carrier in the formulation will typically depend on the other components and amounts of components in the formulation. Furthermore, the type of desired functional and mechanical properties of the formulation as more fully described below will also determine the amount of cosmetic carrier desired in the formulation.

Typically, the cosmetic carrier will be present in the formulation in an amount of from about 0.1% (by weight formulation) to about 95% (by weight formulation). More suitably, the cosmetic carrier is present in an amount of from about 5% (by weight formulation) to about 50% (by weight formulation), and even more suitably, from about 15% (by weight formulation) to about 35% (by weight formulation).

The formulation may further include other components to provide one or more functional, aesthetic, or mechanical benefits to the formulation and, ultimately, to the user of the formulation and substrate having the formulation thereon. Exemplary optional components may include for example: emulsifiers, emollients; skin barrier enhancers; humectants; rheology enhancers; and combinations thereof. Emulsifiers can be included when the formulation is an emulsion formulation. Generally, emulsifiers assist with the formation of a stable emulsion upon contact of the formulation with moisture. Typically, emulsifiers are molecules with non-polar and polar regions that are able to reside at the interface of the water and oil components of the emulsion.

Emulsifiers according to the present disclosure are not particularly limited and will preferably have a hydrophilic/lipophilic balance (HLB) of from 3 to 8, and behave as water-in-oil, oil-in-water, water-in-silicone emulsifiers. Any suitable emulsifier may be included in the formulations of the present disclosure including carbon based emulsifiers, silicon based emulsifiers, non-ionic emulsifiers, cationic emulsifiers, and combinations thereof. Suitable carbon based emulsifiers include polyglyceryl-4 isostearate. Silicon based water-in-oil emulsifiers include alkylene oxide graft modified silicone oils. Suitable alkylene oxides include ethylene oxide, propylene oxide, butylene oxide, and mixtures thereof. Grafting of alkylene oxide groups may occur randomly or in blocks. Preferably, the grafting is block grafting of ethylene oxide and propylene oxide in a weight ratio of 10 to 1. Other emulsifiers include Bis-PEG/PPG-14/14 dimethicone (ABIL® EM 97, available from Evonik), polyglyceryl-3 oleate (ISOLAN® GO 33, available from Goldschmidt), polyglyceryl-4 diisostearate/polyhydrosysteate/sebacate (ISOLAN® GPS, available from Goldschmidt), polyglyceryl-2 dipolyhydroxystearate, polyglyceryl-3 polyricinoleate, PEG-30 dipolyhydroxystearate, glyceryl stearate, hydrogenated vegetable glycerides phosphate, soribitan oleate, sorbitan sessquioleate, sorbitan isostearate, sorbitan trioleate, polyglyceryl-3 -diisostearate, polyglyceryl-4 oleate, or combinations thereof.

The emulsifier may be used alone, or in combination with other emulsifiers. Preferably, the emulsifier is a mixture of polyglyceryl-4 isostearate, cetyl PEG/PPG-10/1 dimethicone, and hexyl laurate, sold under the trademark ABIL® WE 09 (available from Evonik).

The amount of emulsifier in the formulation is not particularly limited and will typically depend upon the emulsion to be made and the end desired functional properties of the formulation.

Emollients lubricate, sooth, and soften the skin surface. Exemplary emollients include oily or waxy ingredients such as esters, ethers, fatty alcohols, hydrocarbons, silicones, and the like, and combinations thereof.

Skin barrier enhancers, also referred to as occlusive materials, increase the water content of the skin by blocking water evaporation. These materials generally include lipids which tend to remain on the skin surface or hydrocarbons such as petrolatum and wax.

Humectants are hydroscopic agents that are widely used as moisturizers. Their function is to prevent the loss of moisture from the skin and to attract moisture from the environment. Common humectants include, for example, glycerin, butylene glycol, betaine, sodium hyaluronate, and the like, and combinations thereof.

Rheology enhancers may help increase the melt point viscosity of the formulation so that the formulation readily remains on the surface of the substrate and/or laminated article and does not substantially migrate into the interior of the substrate, while substantially not affecting the transfer of the formulation to the skin. Additionally, the rheology enhancers help the formulation to maintain a high viscosity at elevated temperatures, such as those encountered during storage and transportation.

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers. Other suitable examples of oil-soluble rheology enhancers include, but are not limited to, aluminum stearate, aluminum tristearate, arachidyl alcohol, arachidyl behenate, behenyl alcohol, $C_{8-22}$ alkyl acrylate/butyl dimethicone methacrylate copolymer, $C_{12-22}$ alkyl acrylate/hydroxyethylacrylate copolymer, $C_{18-38}$ alkyl, $C_{24-54}$ acid ester, $C_{20-24}$ alkyl dimethicone, $C_{24-28}$ alkyl dimethicone, $C_{30-60}$ alkyl dimethicone ceresin, cerotic acid, cetearyl alcohol, cetearyl dimethicone/vinyl dimethicone crosspolymer, cetyl alcohol, cetyl glycol, dibehenyl fumarate, hydrogenated polyisobutene, hydrogenated oils, isocetyl alcohol, isocetyl stearoyl stearate, isophthalic acid/pentaerythritol crosspolymer benzoate/isostearate, isostearyl alcohol, isostearyl stearoyl stearate, jojoba alcohol, lanolin alcohol, lanolin wax, neopentyl glycol dicaprate, neopentyl glycol dicaprylate/dicaprate, neopentyl glycol dicaprylate/dipelargonate/dicaprate, neopentyl glycol diethylhexanoate, neopentyl glycol diheptanoate, neopentyl glycol diisostearate, neopentyl glycol dilaurate, ozokerite, palm alcohol, palm kernel alcohol, paraffin, pentaerythrityl tetramyristate, pentaerythrityl tetraoleate, pentaerythrityl tetrapelargonate, pentaerythrityl tetrastearate, pentaerythrityl trioleate, silica, synthetic beeswax, synthetic candelilla wax, synthetic carnauba, vinyldimethyl/trimethylsiloxysilicate, stearyl dimethicone crosspolymer VP/eicosene copolymer and VP/hexadecene copolymer. Water soluble or water dispersable rheology modifiers include, but are not limited to, acetamide MEA, acrylamide/ethalkonium chloride acrylate Copolymer, acrylamide/ethyltrimonium chloride acrylate/ethalkonium chloride acrylate copolymer, acrylamides copolymer, acrylamide/sodium acrylate copolymer, acrylates/acetoacetoxyethyl methacrylate copolymer, acrylates/beheneth-25 methacrylate copolymer, acrylates/$C_{10-30}$ alkyl acrylate crosspolymer, acrylates/ceteth-20 itaconate copolymer, acrylates/ceteth-20 methacrylate copolymer, acrylates/laureth-25 methacrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/vinyl neodecanoate crosspolymer, acrylic acid/acrylonitrogens copolymer, agar, agarose, algin, alginic acid, ammonium acryloyldimethyltaurate/vinyl formamide copolymer, ammonium acryloyldimethyltaurate/VP copolymer, ammonium alginate, ammonium chloride, amylopectin, avena sativa (oat) kernel flour, bentonite, calcium alginate, calcium carrageenan, $C_{20-40}$ alkyl stearate, carbomer, carboxybutyl chitosan, carboxymethyl hydroxyethylcellulose, carboxymethyl hydroxypropyl guar, cassia Gum, cellulose gum, cetyl hydroxyethylcellulose, $C_{12-14}$ hydroxyalkyl, hydroxyethyl sarcosine, cocamide DEA, cocamide MEA, decyl HDI/PEG-180 crosspolymer, decyltetradeceth-200 isostearate, dextrin, dimethicone/PEG-10 crosspolymer, dimethicone/PEG-15 crosspolymer, dimethylacrylamide/ethyltrimonium chloride methacrylate copolymer, disteareth-75 IPDI, disteareth-100 IPDI, gelatin, gellan gum, hectorite, hydrated silica, hydrolyzed cellulose gum, hydroxybutyl methylcellulose, hydroxyethylcellulose, hydroxyethyl ethylcellulose, hydroxypropyl chitosan, hydroxypropyl guar, hydroxypropyl methylcellulose, hydroxypropyl methylcellulose stearoxy ether, hydroxypropyl starch, hydroxypropyl starch phosphate, hydroxypropyl xanthan gum, isopolyglyceryl-3 dimethicone, isopolyglyceryl-3 dimethiconol, lauryl hydroxysultaine, lauryl/myristyl glycol hydroxypropyl ether, lauryl PEG-9 polydimethylsiloxyethyl dimethicone, lauryl polyglyceryl-3 polydimethylsiloxyethyl dimethicone, levan, magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, myristamidopropyl hydroxysultaine, oatamidopropyl betaine, octacosanyl glycol isostearate, octadecene/MA copolymer, pectin, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14MPEG-20M, PEG-23M, PEG-25M, PEG-45M, PEG-65M, PEG-90M, PEG-115M, PEG-160M, PEG-180M, PEG-120 methyl glucose triisostearate, PEG-120 methyl glucose trioleate, PEG-150 pentaerythrityl tetrastearate, PEG/PPG-120/10 trimethylolpropane trioleate, PEG/PPG-120/10 trimethylpropane trioleatePEG-150/stearyl alcohol/SMDI copolymer, polyacrylate-3, polyacrylate-10, polyacrylate-11, polyacrylic acid, polycyclopentadiene, polyester-S, polyether-1, polyethylene/isopropyl maleate/MA copolyol, polyglycerin-20, polyglycerin-40, polyglyceryl-3 disiloxane dimethicone polyglyceryl-3 polydimethylsiloxyethyl dimethicone, polyquaternium-86, polyvinyl alcohol, potassium polyacrylate, potato starch modified, PVP montmorillonite, sodium acrylates/acrylonitrogens copolymer, sodium acrylates copolymer, sodium acrylates crosspolymer, sodium acrylate/sodium acrylamidomethylpropane sulfonate copolymer, sodium acrylate/sodium acryloyldimethyl taurate/acrylamide copolymer, sodium acrylates/vinyl isodecanoate crosspolymer, sodium acrylate/vinyl alcohol copolymer, sodium acryloyldimethyl taurate/acrylamideNVP copolymer, sodium carboxymethyl beta-glucan, sodium carboxymethyl starch, sodium carrageenan, sodium cellulose sulfate, sodium chloride, sodium hydroxypropyl starch phosphate, sodium isooctylene/MA copolymer, sodium polyacrylate, sodium silicoaluminate, sodium starch octenylsuccinate, sodium sulfate, steareth-100/PEG-136/HDI copolymer, tapioca starch, TEA-alginate, TEA-carbomer, trehalose hydroxypropyltrimonium chloride, tridecyl alcohol, undecyl alcohol, wheat germamidopropyl betaine, xanthan gum, yeast, polysaccharides, and *Zea Mays* (corn) starch.

Still other optional components that may be desirable for use with the formulation of the present disclosure include those cosmetic and pharmaceutical ingredients commonly used in the skin care industry. Examples include abrasives, absorbents, aesthetic components (fragrances, pigments, colorings/colorants), essential oils, skin sensates, astringents (e.g., clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, preservatives, drug astringents, external analgesics, film formers, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents, skin soothing and/or healing agents (e.g., panthenol and derivatives thereof), aloe vera, pantothenic acid and derivatives thereof, allantoin, bisabolol, dipotassium glycyrrhizinate, skin treating agents, sunscreens, thickeners, and vitamins, and combinations thereof. Examples of these and other agents are disclosed in The CTFA Cosmetic Ingredient Handbook, 12$^{th}$ Ed. (2007), which is hereby incorporated by reference to the extent that it is consistent herewith.

The amounts of the optional components will depend on the cosmetic carriers used and the amounts of the cosmetic carriers in the formulations as well as the desired benefits of the formulations.

As noted above, the formulations used in the substrates and articles of the present disclosure typically include greater than 5% (by weight formulation) water, and preferably, are emulsion formulations. More suitably, the formulations include greater than about 10% (by weight formulation) water, even more suitably, greater than about 50% (by weight formulation) water; and even more suitably, greater than about 65% (by weight formulation) water.

Suitable emulsion formulations include, for example, water-in-silicone formulations, water-in-oil emulsions, and oil-in-water emulsions. Also suitable are emulsions within emulsions, such as water-in-oil-in-water emulsions and the like. Particularly preferred are water-in-silicone emulsions.

The amount of water in the emulsions will vary depending on the type of emulsion, specifically, on the type of emulsifier used and the type of oil chosen. Suitably, when the formulation is an emulsion, the emulsion is made of from about 50% to about 85% w/w water. More suitably, the emulsion is made of from about 65% to about 75% w/w water.

Typically, the formulation is applied to the surface of the substrate and will be present in an amount of at least about 10% w/w of the substrate. More suitably, the formulation will be applied to the substrate from about 50% w/w to about 300% w/w; even more suitably, from about 50% w/w to about 200% w/w; and even more suitably, from about 50% w/w to about 100% w/w.

Physical Functional and Mechanical Properties of the Formulations and Substrates Having the Formulations Applied Thereon Surprisingly, it has been found that any of the above-described carriers, used alone or with the optional components, provide an overall formulation for use with the substrates and/or articles of the present disclosure that has a transfer rate of at least about 25% when the viscosity of the formulation is 8,000 cP or greater. More suitably, the formulation should have a transfer rate of at least about 50% when the viscosity of the formulation is 8,000 cP or greater. Specifically, with the above-described cosmetic carriers, it has been found that formulations are produced that are capable of transferring with greater efficiency as compared to formulations including conventional mineral oils.

To determine transfer rate of the formulation, the formulation is first applied to the substrate of interest within conditions specified by the Technical Association of the Pulp and Paper Industry (i.e., at 50% relative humidity and 73° F. (22.8° C.)) (TAPPI). The substrate of interest has been previously cut to a 2-inch diameter circle using an appropriately shaped die and pneumatic press. The formulation (100% w/w) is applied to the substrate with a pipette and spread to ensure a uniform coating as described in WO 2007/018822A1, which is incorporated herein by reference to the extent that it is consistent herewith. After a 12 to 24 hour acclimation period in TAPPI conditions, the sample weight is recorded. The sample is then placed in between six layers of Scott brand paper toweling that is approximately 11 inches in length on any given side and a Plexiglas plate (10.5 inches diameter). A weight sufficient to provide a 0.06 psi load, including the weight of plate, is then distributed across the plate and allowed to remain for approximately fifteen minutes. Following the load, the sample substrate is weighed and the percent weight loss is calculated. The percentage of weight loss was assumed to be the percent transferred to the paper towel. Typically, six specimens may be used for each test material of interest within the method described above.

Having described the disclosure in detail, it will be apparent that modifications and variations are possible without departing from the scope of the disclosure defined in the appended claims.

EXAMPLE

The following non-limiting example is provided to further illustrate the present disclosure.

Example 1

In this Example, various formulations were applied to four separate substrates and/or laminated articles. The degree of transfer of the formulations from the substrates were then determined.

The four substrate samples include (1) a spunbond-filament-spunbond laminate (SFS/Laminate); (2) a Kraton substrate; (3) a FIDO vertical filament laminate; and (4) a Goodnites® boxer absorbent article (commercially available from Kimberly Clark Worldwide, Inc., Neenah, Wis.). The SFS/laminated article sample (140 gsm) was made by sandwiching an elastomeric film substrate between two 50% necked spunbond nonwoven substrates of 0.75 osy each. The elastomeric film layer was comprised of 96% by weight Vistamaxx 1100 resin (commercially available from ExxonMobil, Houston, Tex.) and 4% by weight SCC 11692 white PE resin, which is a filler compound available from Standridge Color Corp. (Social Circle, Ga.), which contains calcium carbonate blended with polypropylene and polypropylene random copolymers. The substrates were thermally point bonded together and allowed to retract to give a 3-D texture. The FIDO laminated article sample (118.87 gsm) was made by sandwiching an elastomeric film substrate (commercially available as Triblock (Kraton MD6688) from Kraton) between two spunbond nonwoven substrate, 0.41 and 0.42 osy respectively. The substrates were adhesively bonded using 2.5 grams/meter$^2$ of a rubber based hot melt adhesive (available as H2808-07 from Bostik Findley).

The water/silicone emulsion formulations for application are shown below.

Water/Silicone Emulsion

| Supplier | Tradename | INCI name | Weight (%) | Weight (g) |
|---|---|---|---|---|
| Phase A | | | | |
| NA | NA | Water | 35.1 | 157.95 |
| COGNIS Co. (Cincinnati, Ohio) | Elestab FL-15 | Butylene Glycol, Glycerin Methylparaben, Chlorophenesin | 2.0 | 9.0 |
| Mallinckrodt (St. Louis, Missouri) | NA | Magnesium Sulfate Heptahydrate | 0.8 | 3.6 |
| Rita (Washington DC) | NA | Propylene Glycol | 5.0 | 22.5 |
| Dow Chemical (Joliet, Illinois) | Versene NA2 | Disodium EDTA | 0.1 | 0.45 |
| Phase B | | | | |
| Dow Corning (Midland, Michigan) | DC 200 10 cst | Dimethicone | 50 | 225 |
| Barnet (Herfordshire, UK) | NET-WO | Cyclopentasiloxane, PEG-10 Dimethicone, Distearyldimonium Hectorite | 7.0 | 31.5 |
| Total | | | 100 | 450 |

To prepare the water/silicone emulsion, the water was warmed to a temperature of about 122° F. (50° C.). The remaining ingredients of Phase A were then mixed until uniform. NET-WO was then dispersed into the DC 200 10 cst at a temperature of 122° F. (50° C.), and Phase A was added to Phase B under gradual homogenization (approximately 10 to 15 grams at a time). The phases were mixed until the free liquid was fully incorporated into the formulation. The formulation was allowed to cool to room temperature and then homogenized again. The formulation had a measured viscosity of 8,000 cP using spindle 95 at 12 rpm, using a Brookfield DV-II+ Pro available from Brookfield Instruments (Middleboro, Mass.). The formulation's dielectric constant of 6.80 was obtained 24 hours following batching using the BI-870 meter available from Brookhaven Instruments Corporation (Holtsville, N.Y.).

The Global glove/sock formulation used in the Example is prepared as follows:

Global Glove/Sock Formulation

| Trade Name | INCI Name | Weight (%) | Weight (g) |
|---|---|---|---|
| NA | Water | 71.9 | 359.5 |
| Versene NA2 (Dow Chemical (Joliet, Illinois)) | Disodium EDTA | 0.1 | 0.5 |
| Betafin BP-20 | Betaine | 2.0 | 10 |
| NA | D,L Panthenol | 0.5 | 2.5 |
| NA | Glycerin | 2.0 | 10 |
| NA | 1,3 Butylene glycol | 3.0 | 15 |
| Cosmedia SP | Sodium Polyacrylate | 0.8 | 4.0 |
| Emulgade CM | Cetearyl isononanoate, Ceteareth-20, Cetearyl alcohol, Glyceryl stearate, Glycerin, Ceteareth-12, Cetyl palmitate, Water | 15 | 75 |
| Paragon MEPB | Phenosyethanol, Methylparaben, Butylparaben, Ethylparaben, Propylparaben | 1.2 | 6.0 |
| Tinoderm A | Retinyl Palmitate, Caprylic/Capric Triglyceride, Polysorbate 80, Lecithin, WAter | 0.5 | 2.5 |
| Tinoderm E | Tocopheryl Acetate, Caprylic/Capric Triglyceride, Polysorbate 80, Lecithin, Water | 0.5 | 2.5 |
| Actiphyte of Aloe Vera extract 10 fold BG50P | Butylene Glycol, Water, Phenoxyethanol, Methylparaben, Ethylparaben, Propylparaben, Butylparaben, Isobutylparaben, Aloe Barbadensis, Leaf extract | 0.5 | 2.5 |
| Actiphyte of Avocado fold BG50P | utylene Glycol, Water, Phenoxyethanol, Methylparaben, Ethylparaben, Propylparaben, Butylparaben, Isobutylparaben, *Persea Gratissima* (avocado) fruit extract | 0.25 | 1.25 |
| Actiphyte of Jojoba Meal fold BG50P | utylene Glycol, Water, Phenoxyethanol, Methylparaben, Ethylparaben, Propylparaben, Butylparaben, Isobutylparaben, *Simmondsia Chinensis* (jojoba) seed extract | 0.25 | 1.25 |
| Madarin & Ginger Flower 178470B | Fragrance | 1.5 | 7.5 |
| Total | | 100 | 500 |

To prepare the Global glove/sock formulation, water is added to Betafin BP20 and Panthenol and mixed until uniform. In a separate container, glycerin, butylene glycol, and Cosmedia SP were mixed until uniform and then added to the Betafin BP20/Panthenol/Water mixture. Emulgade CM is then added and mixed. Then, in order, Paragon MEPB, Tinoderm A, Tinoderm E, Aloe Vera, Avocado, Jojoba Meal, and fragrance was added and mixed until uniform. The pH of the formulation was then adjusted to approximately 5.6 to 6.0, if necessary. The Global glove/sock formulation is further commercially available from Kimberly-Clark Worldwide, Inc. (Neenah, Wis.). The formulation had a measured viscosity of 20,230 cP using spindle 95 at 12 rpm with a Brookfield DV-11+ Pro available from Brookfield Instruments (Middleboro, Mass.). The formulation's dielectric constant of 44.0 was obtained 24 hours following batching using the BI-870 meter available from Brookhaven Instruments Corporation (Holtsville, N.Y.).

The mineral oil was prepared by mixing the following ingredients until uniform.

Mineral Oil Gel Formulation

| Supplier | Tradename | INCI Name | Weight (%) | Weight (g) |
|---|---|---|---|---|
| Penreco (Dickinson, Texas) | Versagel M500 | Mineral Oil and Ethylene/Propylene/Styrene Copolymer and Butylene/Ethylene/Styrene Copolymer | 42.3 | 55.0 |
| COGNIS Co. (Cincinnati, Ohio) | NA | Isopropyl Palmitate | 42.3 | 55.0 |

-continued

Mineral Oil Gel Formulation

| Supplier | Tradename | INCI Name | Weight (%) | Weight (g) |
|---|---|---|---|---|
| ExxonMobil Chemical Co. (Houston, Texas) | PureSyn8 | Hydrogenated polydecene | 11.5 | 15.0 |
| Innospec Chemical (Germany) | Finsolv TN | C12-15 Alkyl Benzoate | 1.9 | 2.5 |
| Arch Personal Care Products (South Plainfield, New Jersey) | Viscup 160 | Mineral Oil and Hydrogenated Styrene/Butadiene Copolymer | 1.9 | 2.5 |
| Total | | | 100 | 130 |

The formulation had a measured viscosity of from about 6,950 to about 7,100 cP using spindle 95 at 12 rpm with a Brookfield DV-11+ Pro available from Brookfield Instruments (Middleboro, Mass.). The formulation's dielectric constant of 4.73 was obtained 24 hours following batching using the BI-870 meter available from Brookhaven Instruments Corporation (Holtsville, N.Y.).

The dielectric constants and transfer efficiencies of the various formulations and components used in the above-described formulations are shown in Table 1.

TABLE 1

| Ingredients | Dielectric Constant ($\varepsilon_r$) | Transfer Efficiency | Standard Deviation |
|---|---|---|---|
| Dimethicone 10 cst | 2.65 | 68.90 | 15.98 |
| Dimethicone 100 cst | 2.65 | 59.44 | 3.66 |
| Dimethicone 350 cst | 2.65 | 39.93 | 14.28 |
| DC 1501 Fluid | NA | 24.63 | 6.06 |
| DC 200 30,000 cst | NA | 13.45 | 2.80 |
| Isopropyl Palmitate | 3.1 | 16.30 | 12.89 |
| Mineral Oil | 2.1 | 33.30 | 4.22 |
| PEG-5 Methyl Ether | 13 | 83.45 | 6.01 |
| PPG-3 Benzyl Ether Myristate | 4.5 | 76.43 | 7.69 |
| Propylene Glycol | 32 | 87.44 | 8.17 |
| Global Glove Sock Formulation | 44 | 24.35 | 0.72 |

The various formulations shown in Table 2 were applied to the samples and the transfer rates for the formulations were determined using the methods described herein. The results are shown in Table 2.

TABLE 2

| Formulation | SFS/Laminate (% transfer) | Kraton (% transfer) | FIDO (% transfer) | BINGO (% transfer) |
|---|---|---|---|---|
| Water-in-silicone Emulsion (50% 10 cst dimethicone) | 34.32 (±4.74) | 41.79 (±4.83) | 69.32 (±1.52) | 36.15 (±3.33) |
| Mineral Oil Gel | 19.94 (±4.24) | 24.00 (±5.67) | 17.28 (±4.00) | 9.95 (±5.73) |
| Global Glove Sock Formulation | 24.35 (±0.72) | — | — | — |

As shown in Table 2, while the expected inverse relationship between viscosity and transfer efficiency was observed as evidenced within the varying grades of dimethicone, the viscosity of the formulations, however, did not account for all differences in transfer efficiency as many of the above-formulations with similar viscosities have drastically different transfer rates. Specifically, as shown in Table 2, it was surprisingly found that while the water-in-silicone emulsion consisting of 50% 10 cst dimethicone had a significantly greater transfer rate as compared to the mineral oil gel on all four substrates even though both formulations had comparable viscosities and dielectric constants and should have transferred at the same rate.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations and substrates/articles without departing from the scope of the disclosure, it is intended that all matter contained in the above description shall be interpreted as illustrative and not in a limiting sense.

What is claimed is:

1. An elastomeric substrate comprising a formulation comprising from 15% to 60% (by weight formulation) of dimethicone silicone oil, wherein the dimethicone silicone oil has a viscosity of from 10 cst to 8,000 cst, and from 5% to 40% (by weight formulation) of water, wherein the formulation has a transfer rate of at least 25% when the viscosity of the formulation is 8,000 cP or greater.

2. The elastomeric substrate as set forth in claim 1 wherein the substrate includes at least 10% w/w formulation.

3. The elastomeric substrate as set forth in claim 1 wherein the formulation is a water-in-silicone emulsion.

4. The elastomeric substrate as set forth in claim 1 wherein the formulation comprises from 15% to 57% (by weight formulation) of dimethicone silicone oil.

5. The elastomeric substrate as set forth in claim 1 wherein the formulation comprises from 15% to 35% (by weight formulation) of dimethicone silicone oil.

6. The elastomeric substrate as set forth in claim 4 wherein the formulation further comprises cyclopentasiloxane, PEG-10 dimethicone and distearyldimonium hectorite.

7. The elastomeric substrate as set forth in claim 1 wherein the formulation comprises from 45% to 50% (by weight formulation) of dimethicone silicone oil and from 30% to 40% (by weight formulation) of water.

8. The elastomeric substrate as set forth in claim 1 wherein the dimethicone silicone oil has a viscosity of from 10 cst to 350 cst.

* * * * *

UNITED STATES PATENT AND TRADEMARK OFFICE
CERTIFICATE OF CORRECTION

PATENT NO. : 9,949,906 B2
APPLICATION NO. : 12/172049
DATED : April 24, 2018
INVENTOR(S) : Stacy Averic Mundschau et al.

It is certified that error appears in the above-identified patent and that said Letters Patent is hereby corrected as shown below:

In the Specification

Column 16, Line 50, delete "polyester-S" and insert therefor -- polyester 5 --.

Column 16, Line 62, delete "taurate/acrylamideNVP" and insert therefor -- taurate/acrylamide/VP --.

Signed and Sealed this
Tenth Day of July, 2018

Andrei Iancu
*Director of the United States Patent and Trademark Office*